United States Patent
Beard

(10) Patent No.: US 7,301,337 B2
(45) Date of Patent: Nov. 27, 2007

(54) FREQUENCY DITHERING TO AVOID EXCITATION PULSE RINGING

(75) Inventor: David Beard, Houston, TX (US)

(73) Assignee: Baker Hughes Incorporated, Houston, TX (US)

(*) Notice: Subject to any disclaimer, the term of this patent is extended or adjusted under 35 U.S.C. 154(b) by 817 days.

(21) Appl. No.: 10/675,187

(22) Filed: Sep. 30, 2003

(65) Prior Publication Data

US 2005/0068027 A1    Mar. 31, 2005

(51) Int. Cl.
*G01V 3/00* (2006.01)
(52) U.S. Cl. .................................... 324/303
(58) Field of Classification Search ............... 324/303
See application file for complete search history.

(56) References Cited

U.S. PATENT DOCUMENTS

| | | | | |
|---|---|---|---|---|
| 6,049,205 | A * | 4/2000 | Taicher et al. | 324/303 |
| 6,121,774 | A | 9/2000 | Sun et al. | 324/303 |
| 6,204,663 | B1 * | 3/2001 | Prammer | 324/303 |
| 6,452,389 | B1 * | 9/2002 | Edwards | 324/303 |
| 6,466,013 | B1 | 10/2002 | Hawkes et al. | 324/303 |
| 6,498,484 | B1 | 12/2002 | Sun et al. | 324/303 |
| 6,541,969 | B2 * | 4/2003 | Sigal et al. | 324/303 |
| 6,559,640 | B2 * | 5/2003 | Taicher | 324/303 |
| 6,570,381 | B1 | 5/2003 | Speier et al. | 324/303 |
| 6,600,316 | B2 * | 7/2003 | Chen et al. | 324/303 |
| 6,661,226 | B1 * | 12/2003 | Hou et al. | 324/303 |
| 6,838,875 | B2 * | 1/2005 | Freedman | 324/303 |
| 6,856,132 | B2 * | 2/2005 | Appel et al. | 324/303 |
| 6,859,034 | B2 * | 2/2005 | Chen | 324/303 |
| 6,903,547 | B2 * | 6/2005 | Sigal et al. | 324/303 |
| 6,956,371 | B2 * | 10/2005 | Prammer | 324/303 |
| 6,972,564 | B2 * | 12/2005 | Chen et al. | 324/303 |

* cited by examiner

*Primary Examiner*—Brij Shrivastav
*Assistant Examiner*—Dixomara Vargas
(74) *Attorney, Agent, or Firm*—Madan, Mossman & Sriram, P.C.

(57) ABSTRACT

An apparatus and method of obtaining information about a property of interest relating to an earth formation resulting in reduced ringing effects is discussed. A Nuclear Magnetic Resonance (NMR) logging tool is conveyed into a borehole in the earth formation. A first pulse sequence is applied having a first associated measurement frequency, and first NMR signals are measured. The first NMR signals include non-formation signals resulting from an excitation pulse and a refocusing pulse in the first pulse echo sequence. A second and third pulse sequence, at different frequencies from each other and from the first frequency, is applied, and corresponding second and third NMR signals are measured. A phase of the non-formation signals resulting from the first pulse echo sequence and a phase of the non-formation signals resulting from the second and third pulse echo sequences are substantially evenly distributed around a unit circle.

38 Claims, 2 Drawing Sheets

FREQUENCY DITHERING TO AVOID EXCITATION PULSE RINGING

BACKGROUND OF THE INVENTION

1. Field of the Invention

The present invention is in the field of nuclear magnetic resonance (NMR) signal processing used in exploring earth formations. More specifically, the invention relates to data acquisition methods and pulse sequences that eliminate the effects of ringing in received NMR signals.

2. Description of the Related Art

In typical NMR operations, the spins of nuclei polarize along an externally applied static magnetic field, assumed to be in the z-direction. The vector sum of the magnetic moment from individual nuclei is a macroscopic magnetic dipole called the magnetization, $M_0$. The magnetization is normally aligned with the static magnetic field, but this equilibrium situation can be disturbed by a pulse of an oscillating magnetic field (e.g. an RF pulse generated by an RF antenna) which rotates the magnetization away from the static field direction. The length of the RF pulse can be adjusted to achieve a prescribed rotation angle, such as 90°, 180°, etc. After rotating the magnetization away from the static field, two things occur simultaneously. First, the spins precess around the static field at the Larmor frequency, given by $\omega_0 = \gamma B_0$, where $B_0$ is the strength of the static field and $\gamma$ is the gyromagnetic ratio. For hydrogen nuclei, $\gamma/2\pi = 4258$ Hz/gauss. So, for example, for a static field of 235 gauss, the frequency of precession would be 1 MHz. Second, the spins return to the equilibrium direction according to a decay time $T_1$, known as the spin-lattice relaxation time. Also associated with the magnetization is a second relaxation called the spin-spin relaxation with a decay time $T_2$.

A widely-used technique for acquiring NMR data both in the laboratory and in well logging uses an RF pulse sequence known as the CPMG (Carr-Purcell-Meiboom-Gill) sequence. As is well-known, after a wait time that precedes each pulse sequence, known as a polarization time, a 90° pulse rotates the magnetization into the x-y plane (transverse plane). This 90° pulse is referred to as a tipping pulse, an excitation pulse or an "A" pulse. Once in the x-y plane, the spins begin to precess around $B_0$ and to lose their relative phase in a process known as dephasing. After a certain time delay, a 180° pulse is applied to cause the spins that are dephasing in the transverse plane to refocus. This 180° pulse is referred to as a flipping pulse, a refocusing pulse or a "B" pulse. Refocusing creates an echo that can be detected by the NMR instrument. By repeated application of the 180° pulse, each application separated by an interecho spacing (TE), a series of "spin echoes" appear, and this series of echoes can be measured and processed. The interecho spacing is typically twice the delay between the 90° pulse and the 180° pulse.

Ringing is a problem encountered when using pulsed NMR techniques. "Ringing" is defined as the presence of a signal appearing in an echo detector window of the NMR tool during the pulsing process, the echo originating from energy stored in some storage means (e.g. electrical or acoustic). In a linear system, the ringing is the sum of signals created by all previous pulses, i.e. by preceding excitation and refocusing ("A" and "B") pulses.

Techniques for filtering the ringing generated by B-pulses are well known. One may apply a second pulse sequence, where the polarity of the A-pulse is alternated in the second pulse sequence. Alternating the polarity of the A-pulse alternates the polarity of the echo, but does not change the polarity of the B-pulse or the ringing due to the B-pulse. Subtracting the two alternated measurements results in a summation of the echo signals and a subtraction of the ringing signals. This technique is called the "phase-alternate pair" (PAP) technique. The PAP technique is generally accepted in the art as a better technique than those that attempt to measure the ringing directly and then to simply subtract it from the entire signal. Simply subtracting the ringing only makes the signal-to-noise ratio worse. Because the PAP technique effectively averages in another echo, the signal-to-noise ratio is improved by a factor of a $\sqrt{2}$. The PAP technique, however, cannot be used to eliminate A-pulse ringing, because the polarity of the A-pulse ringing changes along with the echo.

Another method of eliminating ringing is discussed in U.S. Pat. No. 6,121,774, issued to Sun, et al. Sun '774 advocates measuring the desired echo intensity and the undesired effects during a first pulse sequence. During the single pulse sequence, the spin-echoes, but not the undesired effects, are "spoiled." After spoiling the spin-echoes during the single pulse sequence, the undesired effects are measured and used to correct the first measured spin-echoes and undesired effects in order to eliminate the ringing component. Sun '774 addresses eliminating ringing due to the 180° pulse, and the method may be used to eliminate ringing from pulses of any length. The method taught by Sun '774 is a "spoiling" method that involves skipping a refocusing pulse.

U.S. Pat. No. 6,466,013, issued to Hawkes, et al., discusses a method of using an optimized rephasing pulse sequence. During the applied sequence, a "B" pulse having a spin tip angle substantially less that 180° is applied with carrier phase shifted by typically $\pi/2$ radians with respect to the "A" pulse. Although the refocusing pulses result in spin tip angles of less than 180° throughout the sensitive volume, the RF bandwidth of the "B" pulses is closer to that of the "A" pulse. Hence more of the nuclei originally tipped by the "A" pulse are refocused, resulting in larger echoes than would be obtained with a conventional "B" pulse. The reduced duration of the refocusing pulses also reduces the power consumption of the tool. In one disclosed embodiment, an "A" pulse of inverted phase at the end of the sequence speeds recovery of the longitudinal magnetization by forcing the realignment of the spin system with the static field, enabling cancellation of the tipping pulse "ringing" artifact.

U.S. Pat. No. 6,570,381, issued to Speier, et al., discusses a method of combining a series of cycles of pulse sequences for reducing the effects of ringing. Each of the pulse sequences in Speier '381 includes an RF excitation pulse and several RF refocusing pulses. Spin echo signals are received from the that may include spurious ringing signals from the excitation and refocusing pulses. The spin echo signals are combined from corresponding spin echoes of each of the cycles of pulse sequences to obtain combined spin echo signals in which spurious ringing from the excitation pulses and refocusing pulses of the pulse sequences are substantially cancelled. The steps of producing cycles of pulse sequences and combining spin echo signals include manipulating the polarities of the excitation and refocusing pulses to obtain the substantial cancellation of the spurious ringing from the excitation and refocusing pulses. The disclosure teaches that four cycles of pulse sequences is preferred.

U.S. Pat. No. 6,204,663 to Prammer discusses a method for suppression of magneto-acoustic artifacts in NMR data. In one embodiment at least one first pulse-echo sequence, having a frequency $F_1$, is applied. At least one second pulse-echo sequence, having a frequency $F_2$ which is different from $F_1$, is then applied. The frequency difference is defined as a function of the time delay between excitation pulse and data acquisition, such that:

$$|F_1 - F_2| = \frac{1}{(4\tau)} \quad (1)$$

where τ is the constant delay time both between the excitation pulse and the first refocusing pulse (TE/2) and also between the refocusing pulses and the acquisition windows.

In a more general case, the frequency difference can be expressed as:

$$|F_1 - F_2| = \left(n + \frac{1}{2}\right)\frac{1}{2\tau} \quad (2)$$

in which n is any integer or zero. It will be appreciated that for n=0, Eq. (2) is identical to Eq. (1). The generic Eq. (2) further indicates that a frequency difference corresponding to an additional offset of n/(2τ) will also work due to the cyclic nature of the problem. Since keeping the frequency difference relatively small is desirable, however, the case in which n=0 is preferred. In the Prammer '663 patent only the pulse ringing due to the 90° pulse is removed. A PAP procedure is still needed to remove the ringing from the 180° pulse.

SUMMARY OF THE INVENTION

The present invention is a system and method for obtaining information about an earth formation via nuclear magnetic resonance (NMR) with reduced ringing effects. An NMR logging tool is conveyed into a borehole penetrating an earth formation. The term "earth formation" as used in this application, is used in its commonly-accepted and broad sense, including isotropic and anisotropic formations, regardless of the homogeneity, consistency, thickness or composition of the substance found in the earth.

A first pulse sequence is generated by the tool, the first sequence having a first frequency. First NMR signals corresponding to the first pulse sequence are measured. These first NMR signals include non-formation signals resulting from an excitation pulse and a refocusing pulse within the first pulse echo sequence. A second and third pulse sequence, having frequencies different from each other and from the first frequency, are applied. Corresponding second and third NMR signals resulting from the second and third pulse sequences are measured. From the first, second and third measured NMR signals, a property of the earth formation is determined. The estimate of property is substantially unaffected by non-formation signals.

The term "a property of the earth formation" is used in its broadest sense appreciated in the art. Such a property may include a $T_1$ distribution, porosity, bound fluid volume, bound volume irreducible.

In one mode of the invention, the relationship between the first, second and third frequencies is defined by $$nf \cdot \delta f = \frac{2}{TE} = \frac{1}{TE/2} \quad (3)$$

where nf is the number of frequencies, δf is the separation of frequencies and TE is the interecho spacing. In an alternate mode, the relationship between the first, second and third frequencies is defined by $$nf \cdot \delta f = \frac{1}{TE} \quad (4)$$

where nf is the number of frequencies, δf is the separation of frequencies and TE is the interecho spacing. A phase of the non-formation signals resulting from the first pulse echo sequence and a phase of the non-formation signals resulting from the second and third pulse echo sequences are substantially evenly distributed around a unit circle.

BRIEF DESCRIPTION OF THE DRAWINGS

The invention is described with reference to the following drawings, in which.

DETAILED DESCRIPTION OF THE INVENTION

The system and method of the present invention are suitable for use in wireline exploration. The system and method can also be used effectively in a measurement-while-drilling (MWD) device or any other application in which NMR is used to interrogate an earth formation. The wireline device exemplified in the following detailed description is for purposes of example only and is not intended as a limitation of the scope of the invention or its usefulness.

Figure 1:
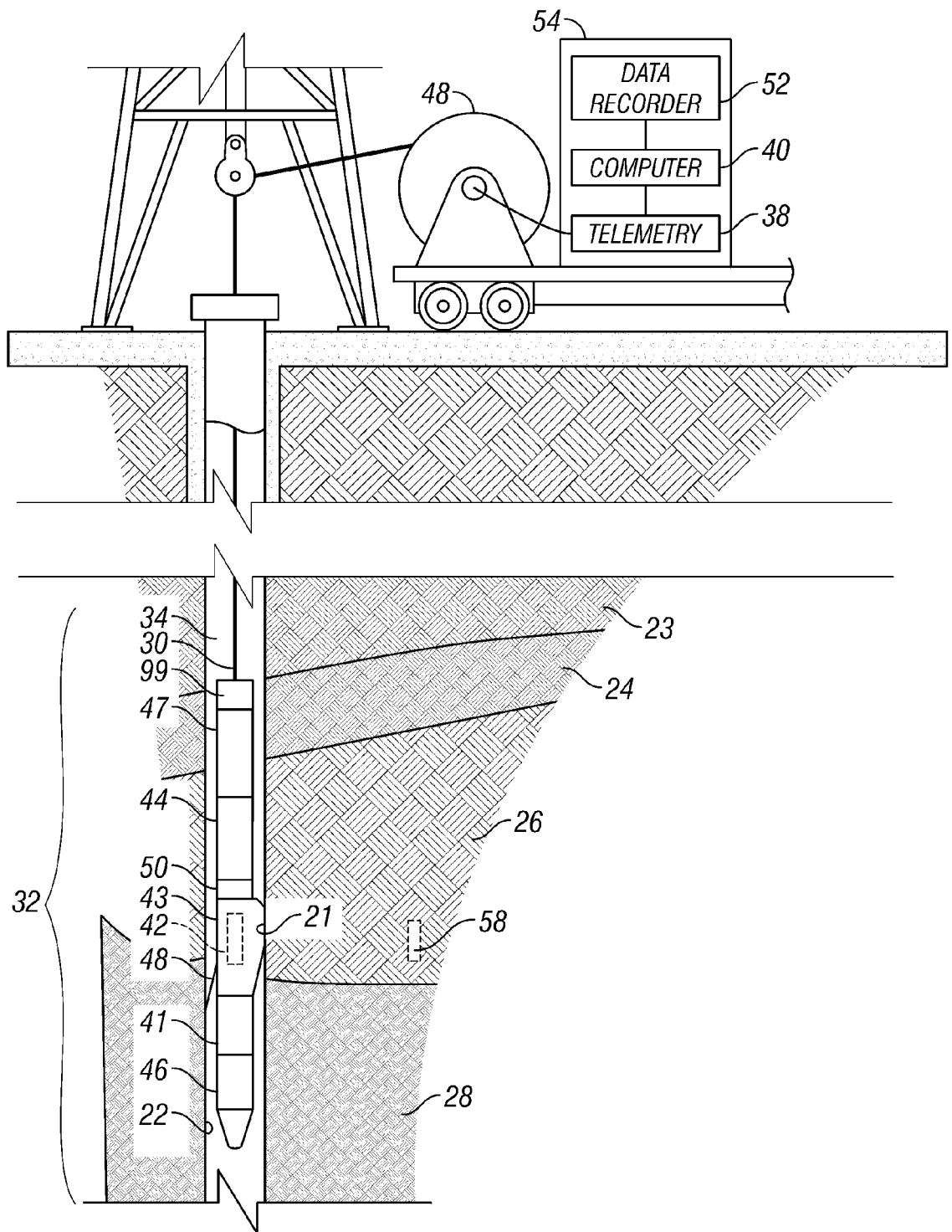
FIG. 1 shows an NMR wireline well-logging apparatus used in conjunction with the present invention.

FIG. 1 shows a string of logging tools 32 disposed in a wellbore 22 drilled through earth formations 23, 24, 26, 28 for the purpose of making measurements of the properties of the earth formations 23, 24, 26, 28. The wellbore 22 is filled with drilling mud 34. A "sensitive volume," 58 generally has the shape of a cylindrical sector and is disposed within one or more of the earth formations 26. The sensitive volume 58 is located on one side of the wellbore 22 and is a predetermined portion of the earth formation 26 in which NMR measurements are to be made.

A string of logging tools 32 includes an NMR logging instrument 42 designed according to the present invention and is lowered into the wellbore 22 by a means of an armored electrical cable 30. The cable 30 may be alternately extended into and withdrawn from the wellbore 22 by means of a winch or drum 48 or similar device known in the art. The tool string 32 may be electrically connected to surface equipment 54 by an insulated electrical conductor (not shown) forming part of the cable 30. The surface equipment 54 may include one part of a telemetry system 38 for communicating control signals and data between the tool string 32 and a computer 40. The computer 40 may also include a data recorder 52 for recording measurements made by the logging apparatus and transmitted to the surface equipment 54 over the cable 30. Alternatively, a downhole processor (not shown) may be used for controlling the operation of the NMR instrument and/or processing of the signals measured by the instrument.

An NMR probe 42 according to the present invention is included in the tool string 32. The NMR probe 42 may have a face 21 designed to be placed in contact with the wellbore 22 wall and having an appropriate curvature so that only a very small gap exists between the face 21 and the wellbore 22 wall. The probe 42 can also have a selectably extensible arm 48 or similar means for extending the probe 42 which may be activated to press the probe 42 in the direction of the wellbore 22 wall, so that the face 21 is firmly pressed against the wellbore 22 wall during measuring operations.

Circuitry for operating the NMR probe 42 may be located within an NMR electronics cartridge 44 or similar facility. The circuitry may be connected to the NMR probe 42 through a connector 50. The NMR probe 42 is may be located within a protective housing 43 which is designed to exclude the drilling mud 34 from the interior of the probe 42.

Other well logging sensors may form part of the tool string 32. As shown in FIG. 1, one of the additional logging sensors 47 may be located above the NMR electronics cartridge 44. Other logging sensors, such as shown at 41 and 46 may be located below the NMR probe 42. The other sensors 41, 46, 47 can be of types familiar to those skilled in the art and can include, but are not limited to, gamma ray detectors, formation bulk density sensors or neutron porosity detectors. Alternatively, parts of the NMR electronics may be located within electronic cartridges which form part of other logging sensors 41, 46, 47. The locations and types of the other sensors 41, 46, 47 shown in FIG. 1 are a matter of convenience for the system designer and are not to be construed as a limitation on the invention.

Figure 1A:
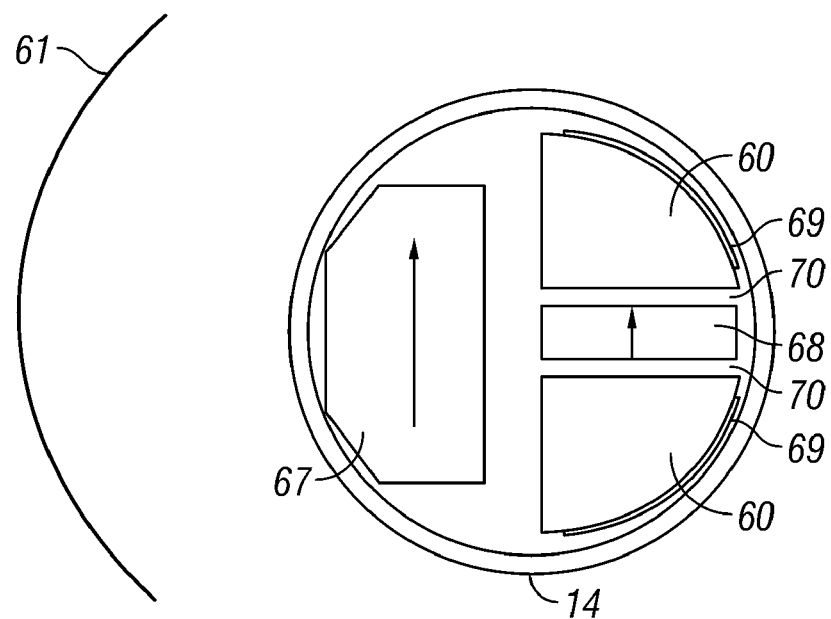
FIG. 1A shows a magnet and antenna configuration of an embodiment of the device used in the present invention.

FIG. 1A schematically illustrates an embodiment of the NMR tool in conformance with the present invention. This portion of the invention is described fully in U.S. Pat. No. 6,348,792 to Beard, et al., having the same assignee as the present invention and the contents of which are fully incorporated herein by reference. It is to be noted that the system and method of the present invention would be equally effective with other prior art devices used for NMR measurements in boreholes. The arrangement of magnets and antennas may be as described herein or may be otherwise configured, as is well appreciated in the art, all falling within the bounds of the instant invention. The tool cross-sectional view in FIG. 1A illustrates a main magnet 67, a second magnet 68, and a transceiver comprises antenna 69 and core material 60. The arrows 71 and 73 depict the polarization (e.g., from the south pole to the north pole) of the main magnet 67 and the secondary magnet 68. A noteworthy feature of the arrangement shown in FIG. 1A is that the polarization of the magnets providing the static field faces the side of the tool, rather than facing the front of the tool (the right side of FIG. 1A) as in prior art devices. The importance of this rotated configuration is discussed below.

The second magnet 68 is positioned so as to augment the shape of the static magnetic field by adding a second magnetic dipole in close proximity to the RF dipole defined by the wires 69 and the soft magnetic core 60. This positioning moves the center of the effective static dipole closer to the RF dipole, thereby increasing the azimuthal extent of the region of examination, the desirability of which has been discussed above. The second magnet 68 also reduces the shunting effect of the high permeability magnetic core 60 on the main magnet 67. In the absence of the second magnet, the DC field would be effectively shorted by the core 60. Thus the second magnet, besides acting to shape the static field to the front of the tool (the side of the main magnet), also acts as a bucking magnet with respect to the static field in the core 60. Those versed in the art will recognize that the bucking function and limited shaping could be accomplished by having a gap in the core. Since some kind of field shaping is required on the front side of the tool, one embodiment of the invention features the second magnet serving both for field shaping and for bucking. If the static field in the core 60 is close to zero, then the magnetostrictive ringing from the core is substantially eliminated.

The frequency dithering technique of the present invention is similar to the PAP technique of prior art in that it seeks to vary the relative phase of the non-formation signal and hence reduce the A-pulse ringing while improving the signal-to-noise ratio. This goal is accomplished under the instant invention by making small changes in the fundamental frequency of the NMR acquisition. The frequency and phase of the echo and the demodulation in the detection system are locked to the fundamental frequency of the pulse. Small changes in frequency cause little or no change in the phase of the detected echo. In gradient field systems, small changes in frequency cause only small changes in the signal amplitude. Therefore, for small changes in frequency (i.e. those much less than the bandwidth of the acquisition), the echo signal is effectively constant. The frequency of the non-formation signal, however, is not locked to that of the acquisition. By varying the frequency of the acquisition, the phase of the non-formation signal will change by a determinable amount given by the equation:

$$\delta\phi = 2\pi \cdot \delta f \cdot t \tag{5}$$

where $\delta\phi$ is the change of phase, $\delta f$ is the change in frequency, and t is the time over which the phase difference evolves (i.e. the time between the effective center of the pulse and the effective center of the detection window).

In the method of the present invention, a series of pulse sequences is applied. In one embodiment, a first pulse sequence of excitation and refocusing pulses is applied at an associated first measurement frequency. Measurements are made of the first NMR signals corresponding to the first pulse sequence. The measured signals will comprise spin-echo signals as well as non-formation signals. Next, second and third pulse sequences are applied. The second and third pulse sequences each have associated measurement frequencies different the other measurement frequencies used. The pulse sequences may include a CPMG sequence as known in the art or may include a modified CPMG sequence including a refocusing pulse having a tipping angle less than 180°. Such a modified CPMG pulse sequence is disclosed in U.S. Pat. No. 6,163,153 to Reiderman, et al. Measurements are made of the NMR signals obtained from the formation after the second and third pulse sequences. The three sets of measurements, obtained at three substantially separate frequencies, can then be used to remove non-formation signal from the processed signal.

If the timing between pulses is maintained at a constant, the echo magnitude will be essentially independent of the acquisition frequency. By varying the frequency a small amount in each pulse sequence, one can vary the phase of the non-formation signal while keeping the amplitude of the non-formation signal and the phase and amplitude of the echo constant. It is therefore possible to eliminate the non-formation signal by performing acquisitions at two or more frequencies using frequency separations that will cause the non-formation signal to sum to zero.

If the vectors representing the phase of the non-formation signal are evenly distributed around the unit circle they will sum to zero. That is:

$$\sum_{j=1}^{nf} e^{i \cdot j \cdot \delta\phi} = 0$$

Figure 2:
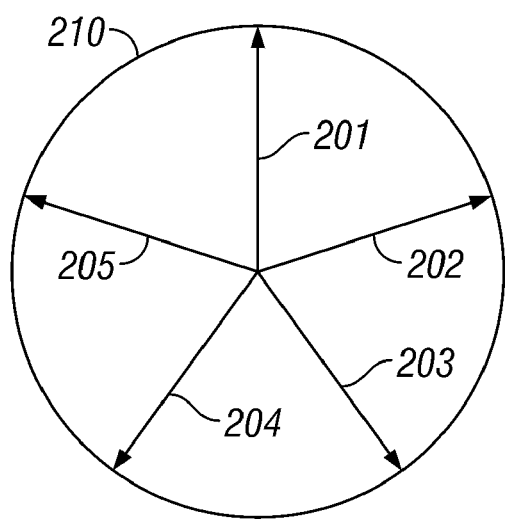
FIG. 2 shows an example of unit vectors evenly distributed about a unit circle.

FIG. 2 shows schematically a selection of five unit vectors, 201, 202, 203, 204 and 205, evenly distributed around a unit circle 210. The illustration shows how five such evenly distributed vectors can sum to zero. The number of vectors in FIG. 2 is chosen for illustrative purposes only and is not meant as a limitation on the present invention. If nf is the number of frequencies used, and the frequencies are separated by steps of size δf, the condition for the non-formation signal to sum to zero is given by the equation:

$$nf \cdot \delta f = \frac{m}{t} \qquad (6)$$

where m is any integer that is not a multiple of nf.

Using the general Eq. (6), it is possible to derive specific cases. The simplest and most practical case is where two frequencies are applied and nf=2, m=1, and t=TE. Setting m=1 minimizes δf, thereby permitting small frequency changes. Noting that TE, the approximate time between an A-pulse and the first echo, is described as 2τ, one obtains the equation:

$$\delta f = \frac{1}{4 \cdot \tau} \qquad (7)$$

Eq. (7) is identical to the equation derived from the technique described in equation (1) of Prammer '663, also referred to as Eq. (1) herein.

In a second and more general case, one can apply two frequencies where m is an odd integer. In this case nf=2, m=2n+1, and t=TE=2τ; where n is an integer. This definition of m ensures that it is not a multiple of 2, thereby leading to a necessary condition for the cancellation as described above. In this second case:

$$\delta f = \left(n + \frac{1}{2}\right) \cdot \frac{1}{2 \cdot \tau} \qquad (8)$$

Eq. (8) is identical to the equation derived from the technique described in equation (1A) of Prammer '663, also referred to as Eq. (2) herein.

In a third case, which is the case of the present invention, three or more frequencies are used, such that nf>2, m=2, and t=TE and TE/2. These parameter assignments in Eq. (6) lead to the equation:

$$nf \cdot \delta f = \frac{2}{TE} = \frac{1}{TE/2} \qquad (9)$$

Eq. (9) shows that when m is 2, and nf>2 (a necessary condition to avoid having m being a multiple of nf) the zero condition is met for evolution times of TE and TE/2. In other words the frequency dithering can be used to eliminate both A-pulse and B-pulse ringing without a PAP. Using three pulse sequences having three separate frequencies (nf=3) enables the elimination of non-formation signals in a reduced time.

Similar reduction conditions can be achieved for any even value of m, but m=2 to date yields excellent satisfactory results. Other (larger) values of m are likely to require variations in frequency that are too large.

The use of three frequencies is a point of novelty not discussed in Prammer '633 and results in a reduction of time over the method of Prammer '633. The same elimination using dithering plus the prior art PAP method, as discussed in Prammer '663 and Speier '381, requires the use of at least four acquisitions. When using the system and method of the present invention in conjunction with a single-frequency measurement device, a user can achieve results free of ringing in a reduced amount of time. Use of the system and method of the instant invention in a multi-frequency measurement device enables further reduction of operation times over that of a single frequency measurement device.

Further operation can be made in a fourth case, with three or more frequencies, with the condition where nf>2, m=1, and t=TE. Such an operating condition leads to the equation:

$$nf \cdot \delta f = \frac{1}{TE} \qquad (10)$$

It may be preferable in certain circumstances to operate at three or more frequencies (nf>2), especially if time is available to apply more than 2 dithering frequencies, e.g. in a package for determination of clay bound water (CBW) that has several CPMG sequences. At nf>2, the operation of reducing the non-formation signal is less effected by errors in the evolution time (t). In practice, it is not trivial to determine the "effective center" of a pulse and the evolution time from that center to the effective center of an acquisition window. For example a 10% error in an estimate of the evolution time will cause a 14% residual non-formation signal if nf=2, but only a 10% residual non-formation signal if nf=6.

In some NMR devices, the frequency can be adjusted with a finite resolution, e.g 100 Hz. For a fixed integer m, as the number of frequencies used increases, the δf becomes smaller. With a smaller δf, issues of finite frequency resolution must be considered. It is more difficult to get close to the correct value of δf, for small values δf, i.e. larger nf. For example, the table below summarizes the effect of 100 Hz discretization on the residual non-formation signal for various nf at TE=0.6 ms.

| | Nf | | | | | | | | | | |
|---|---|---|---|---|---|---|---|---|---|---|---|
| | 2 | 3 | 4 | 5 | 6 | 7 | 8 | 9 | 10 | 11 | 12 |
| err(%) | 6.3 | 0.1 | 4.6 | 11.5 | 7.7 | 18.7 | 4.3 | 7.5 | 16 | 20.9 | 34.3 |

When the resolution of the frequency selection in the NMR instrument is finite, i.e., the frequencies are discretely sampled, it may not be possible to exactly satisfy the condition.

$$\sum_{j=1}^{nf} e^{i \cdot j \cdot \delta \phi} = \sum_{j=1}^{nf} e^{i \cdot j \cdot \pi \cdot \delta f \cdot TE} = 0 \qquad (11)$$

In fact, the frequencies may not even be uniformly spaced. So it becomes necessary to determine the phase shift of each measurement separately, i.e. $\delta \phi_j$. The problem is that in general.

$$\sum_{j=1}^{nf} e^{i\delta\phi_j} \neq 0 \quad (12)$$

However, instead of simply summing the measurements, in one embodiment of the invention, a weighted summation is done. The condition for valid echo measurement and cancellation of ringing become, respectively.

$$\sum_{j=1}^{nf} w_j = 1, \quad \sum_{j=}^{nf} w_j e^{i\delta\phi_j} = 0 \quad (13)$$

These can be rewritten as:

$$\sum_{j=1}^{nf} w_j = 1, \quad \sum_{j=}^{nf} w_j \cos(\delta\phi_j) = 0, \quad \sum_{j=}^{nf} w_j \sin(\delta\phi_j) = 0 \quad (14)$$

It can be seen that we have three equations, so for nf≧3, there is a solution, i.e., there is a set of $w_j$ which will give us an echo measurement free of artifacts. For nf=3, the problem is determined and there is a unique solution. For nf>3, the problem is underdetermined so the solution can be found subject to the additional constraint that the noise in the echo measurement is minimized. That is, $$\sum_{j=1}^{nf} (w_j)^2 = \min \quad (15)$$

For nf=2 this approach cannot be used. Hence there is a definite advantage in using the method of the present invention over a two frequency dithering scheme such as that described in prior art.

After the ringing due to the excitation and refocusing pulses has been removed, prior art methods can be used to determine a property of interest of the earth formation. "Property of interest" is a term well-known in the art to mean a characteristic of a formation and may include, without limitation, a $T_2$ distribution, a $T_1$ distribution, a porosity, a bound fluid volume, or a bound volume irreducible.

The method of the present invention has been described in detail above with reference to a wireline tool. The method is equally applicable using a Measurement-While-Drilling (MWD) tool conveyed on a drilling tubular such as a drillstring or coiled tubing. Similarly, the instrumentation disclosed in this invention and the methods discussed could be used regardless of the actual method of delivery, which could be other than via wireline or MWD, all falling within the bounds of this disclosure.

While the foregoing disclosure is directed to a particular set of embodiments of the invention, various modifications will be apparent to those skilled in the art. It is intended that all such variations within the scope and spirit of the appended claims be embraced by the foregoing disclosure. Similarly, though specifics such as frequencies, orders of operation, and other such exacting specifications are discussed, it will be appreciated that these specifics are provided for the purposes of examples and that many variations of such specifics may be resorted to, all falling within the bounds of the invention.

What is claimed is:

1. A method of estimating a property of interest relating to an earth formation comprising:
   (a) conveying a Nuclear Magnetic Resonance (NMR) logging tool into a borehole in said earth formation;
   (b) applying a first pulse sequence having a first associated measurement frequency and measuring first signals corresponding to said first pulse sequence, said first signals including non-NMR signals resulting from (A) an excitation pulse, and, (B) a refocusing pulse in said first pulse sequence;
   (c) applying a plurality of additional pulse sequences having associated additional frequencies different from each other and from said first frequency;
   (d) measuring additional signals resulting from applying said plurality of additional pulse sequences;
   (e) determining from said first and said additional measured signals an estimate of said property of interest, said estimate substantially unaffected by said non-NMR signals; and
   (f) recording the estimate of the property of interest on a suitable medium;
   wherein the first and the additional frequencies are related by an expression of the form $$nf \cdot \delta f = \frac{m}{t}$$

where δf is a separation of frequencies, nf is the number of frequencies, m is any integer that is not a multiple of nf, and t is a time over which a phase difference evolves.

2. The method of claim 1 wherein said first and said additional frequencies are related by an expression of the form $$nf \cdot \delta f = \frac{2}{TE} = \frac{1}{TE/2}$$

where TE is an interecho spacing.

3. The method of claim 1 wherein said first and said additional frequencies are related by an expression of the form:

$$nf \cdot \delta f = \frac{1}{TE}$$

where TE is an interecho spacing.

4. The method of claim 1 wherein a phase of said non-NMR signals resulting from said first pulse sequence and phases of non-NMR signals resulting from said additional pulse sequences are substantially evenly distributed around a unit circle.

5. The method of claim 1 wherein at least one of said first pulse sequence and said additional pulse sequences comprises a CPMG sequence.

6. The method of claim 5 wherein said first and said additional frequencies are related by an expression of the form:

$$nf \cdot \delta f = \frac{2}{TE} = \frac{1}{TE/2}$$

where nf is the number of frequencies, δf is a separation of frequencies and TE is an interecho spacing.

7. The method of claim 5 wherein said first and said additional frequencies are related by an expression of the form;

$$nf \cdot \delta f = \frac{1}{TE}$$

where nf is the number of frequencies, δf is a separation of frequencies and TE is an interecho spacing.

8. The method of claim 1 wherein at least one of said first pulse sequence and said additional pulse sequences comprises a modified CPMG sequence having a refocusing pulse with a tipping angle of less than 180°.

9. The method of claim 8 wherein said first and said additional frequencies are related by an expression of the form:

$$nf \cdot \delta f = \frac{2}{TE} = \frac{1}{TE/2}$$

where nf is the number of frequencies, δf is a separation of frequencies and TE is an interecho spacing.

10. The method of claim 8 wherein said first and said additional frequencies are related by an expression of the form:

$$nf \cdot \delta f = \frac{1}{TE}$$

where nf is the number of frequencies, δf is a separation of frequencies and TE is an interecho spacing.

11. The method of claim 1 wherein determining the value of said property of interest further comprises summing said first and said additional measured signals.

12. The method of claim 1 wherein said first and said additional signals have a signal loss of less than 0.8% relative to a signal that would be obtained at a nominal frequency corresponding to said first and said additional frequencies.

13. The method of claim 1 wherein the property of interest is at least one of (i) a $T_2$ distribution, (ii) a $T_1$ distribution, (iii) a porosity, (iv) a bound fluid volume, and (v) a bound volume irreducible.

14. The method of claim 1 wherein said first and said plurality of additional frequencies are discretely sampled and wherein determining said value of said property of interest further comprises forming a weighted summation of said measurements at said first and said additional frequencies.

15. The method of claim 14 wherein said forming of said weighted summation further comprises minimizing a noise in an echo measurement.

16. A Nuclear Magnetic Resonance (NMR) apparatus for use in a borehole an earth formation comprising:

(a) a magnet configured to produce a static field in a region of said earth formation, said magnet aligning nuclear spins in said region substantially parallel to a direction of said static field;

(b) a transmitter configured to apply radio-frequency (RF) pulse sequences at each of at least three different frequencies;

(c) a receiver configured to receive at least three signals resulting from said at least three pulse sequences, said at least three signals comprising (A) a non-NMR signal, and, (B) NMR signals resulting from interactions of said RF pulses with the earth formation; and (d) a processor configured to determine from said at least three received signals an estimate of a property of interest of said earth formation, said estimate substantially unaffected by said non-NMR signal wherein said first and said additional frequencies are related by an expression of the form:

$$nf \cdot \delta f = \frac{m}{t}$$

where δf is a separation of frequencies, nf is the number of frequencies, m is any integer that is not a multiple of nf, and t is a time over which a phase difference evolves.

17. The apparatus of claim 16 wherein said at least three frequencies are related by an expression of the form:

$$nf \cdot \delta f = \frac{2}{TE} = \frac{1}{TE/2}$$

where nf is the number of frequencies, δf is a separation of frequencies and TE is an interecho spacing.

18. The apparatus of claim 16, wherein at least three frequencies are related by an expression of the form:

$$nf \cdot \delta f = \frac{1}{TE}$$

where nf is the number of frequencies, δf is a separation of frequencies and TE is a interecho spacing.

19. The apparatus of claim 16, wherein phases of said non-NMR signals resulting from said at least three pulse sequences are substantially evenly distributed around a unit circle.

20. The apparatus of claim 16 wherein at least one of said three pulse sequences comprises a CPMG sequence.

21. The apparatus of claim 20 wherein said at least three frequencies are related by an expression of the form:

$$nf \cdot \delta f = \frac{2}{TE} = \frac{1}{TE/2}$$

where nf is the number of frequencies, δf is a separation of frequencies and TE is an interecho spacing.

22. The apparatus of claim 20, wherein at least three frequencies are related by an expression of the form:

$$nf \cdot \delta f = \frac{1}{TE}$$

where nf is the number of frequencies, δf is a separation of frequencies and TE is an interecho spacing.

23. The apparatus of claim 16 wherein at least one of said at least three pulse sequences comprises a modified CPMG sequence having a refocusing pulse with a tipping angle less than 180°.

24. The apparatus of claim 23 wherein said at least three frequencies are related by an expression of the form:

$$nf \cdot \delta f = \frac{2}{TE} = \frac{1}{TE/2}$$

where nf is the number of frequencies, δf is a separation of frequencies and TE is an interecho spacing.

25. The apparatus of claim 23, wherein at least three frequencies are related by an expression of the form:

$$nf \cdot \delta f = \frac{1}{TE}$$

where nf is the number of frequencies, δf is a separation of frequencies and TE is an interecho spacing.

26. The apparatus of claim 16 wherein said processor is configured to determine said value by summing said at least three received signals.

27. The apparatus of claim 16 wherein said non-NMR signal is at least one of (A) ringing resulting from an excitation pulse in said RF pulse sequences, and, (B) a ringing resulting from a refocusing pulse in said RF pulse sequences.

28. A system for estimating a property of interest of an earth formation comprising:
 (a) a logging tool including a magnet configured to produce a static field in a region of said earth formation, said magnet aligning nuclear spins in said region substantially parallel to a direction of said static field;
 (b) a transmitter on said logging tool configured to apply radio frequency pulse sequences at each of at least three frequencies;
 (c) a receiver on said logging tool configured to receive signals resulting from interaction of said at least three pulse sequences with said earth formation, said signals indicative of a property of said earth formation, said signals including non-NMR signals resulting from an excitation pulse and a refocusing pulse in said at least three pulse sequences;
 (d) a conveyance device configured to convey said logging tool into a borehole in said earth formation;
 (e) a processor in electrical communication with the transmitter and the receiver, said processor programmed to perform steps for determining from said at least three received signals a value of said property of said earth formation, said determined value of said property substantially unaffected by said non-NMR signals;

wherein said at least three frequencies are related by an expression of the form:

$$nf \cdot \delta f = \frac{m}{t}$$

where δf is a separation of frequencies, nf is the number of frequencies, m is any integer that is not a multiple of nf, and t is a time over which a phase difference evolves.

29. The system of claim 28 wherein said conveyance device comprises a wireline.

30. The system of claim 28 wherein said conveyance device comprises a drillstring.

31. The system of claim 28 wherein said conveyance device comprises coiled tubing.

32. The system of claim 28 wherein said processor is programmed to select the at least three frequencies according to an expression of the form:

$$nf \cdot \delta f = \frac{2}{TE} = \frac{1}{TE/2}$$

where nf is the number of frequencies, δf is a separation of frequencies and TE is an interecho spacing.

33. The system of claim 28 wherein said processor is at a surface location.

34. The system of claim 28 wherein said processor is at a downhole location.

35. The system of claim 28 wherein the processor is programmed to instruct the transmitter to transmit at least one of said at least three pulse sequences as a CPMG sequence.

36. The system of claim 28 wherein the processor is programmed to instruct the transmitter to transmit at least one of said at least three pulse sequences as a modified CPMG sequence having a refocusing pulse with a tipping angle less than 180°.

37. The system of claim 28 wherein said processor is programmed to determine said value by summing said at least three received signals.

38. The system of claim 28 wherein said property is at least one of (i) a $T_2$ distribution, (ii) a $T_1$ distribution, (iii) a porosity, (iv) a bound fluid volume, and, (v) a bound volume irreducible.

* * * * *